United States Patent
Isaacson (10) Patent No.: US 11,571,543 B2
(45) Date of Patent: Feb. 7, 2023

(54) CATHETER SYSTEM CLAMP, SYSTEMS, AND METHODS

(71) Applicant: Becton, Dickinson and Company, Franklin Lakes, NJ (US)

(72) Inventor: S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 269 days.

(21) Appl. No.: 16/841,379

(22) Filed: Apr. 6, 2020

(65) Prior Publication Data
US 2020/0316336 A1 Oct. 8, 2020

Related U.S. Application Data

(60) Provisional application No. 62/830,838, filed on Apr. 8, 2019.

(51) Int. Cl.
*A61M 25/00* (2006.01)
*A61M 39/28* (2006.01)
(Continued)

(52) U.S. Cl.
CPC ............ *A61M 25/00* (2013.01); *A61M 5/14* (2013.01); *A61M 39/28* (2013.01); *G16H 10/60* (2018.01); *A61M 2005/1403* (2013.01); *A61M 2025/0019* (2013.01); *A61M 2205/18* (2013.01); *A61M 2205/3327* (2013.01); *A61M 2205/3334* (2013.01); *A61M 2205/3584* (2013.01);
(Continued)

(58) Field of Classification Search
CPC ........ A61M 25/00; A61M 5/14; A61M 39/28; A61M 2005/1403; A61M 2025/0019; A61M 2205/18; A61M 2205/3327; A61M 2205/3334; A61M 2205/3584; A61M 2205/581; A61M 2205/582; A61M 2205/583; A61M 2205/587; A61M 25/0606; G16H 10/60
See application file for complete search history.

(56) References Cited

U.S. PATENT DOCUMENTS

| 5,533,412 A | 7/1996 | Jerman et al. |
| 2005/0055242 A1* | 3/2005 | Bello ............... G16H 20/17 705/2 |

(Continued)

FOREIGN PATENT DOCUMENTS

| WO | 2011/119425 | 9/2011 |
| WO | 2016/057981 | 4/2016 |

(Continued)

*Primary Examiner* — Susan S Su
*Assistant Examiner* — Eric Rassavong
(74) *Attorney, Agent, or Firm* — Kirton Mcconkie; Whitney Blair; Kevin Stinger (57) ABSTRACT

A method to manage flushing of a catheter assembly may include providing a clamp for a fluid tube configured to be coupled to the catheter assembly. The clamp may include a sensor configured to detect the clamp is closed. The method may include starting a timer in response to the sensor detecting the clamp is closed. The method may include providing an alert in response to the timer reaching a predetermined duration of time. The alert may indicate to a clinician that the catheter assembly should be opened and flushed, which may prevent occlusion of the catheter assembly.

15 Claims, 4 Drawing Sheets

(51) Int. Cl.
*A61M 5/14* (2006.01)
*G16H 10/60* (2018.01)
(52) U.S. Cl.
CPC . *A61M 2205/581* (2013.01); *A61M 2205/582* (2013.01); *A61M 2205/583* (2013.01); *A61M 2205/587* (2013.01)

(56) References Cited

U.S. PATENT DOCUMENTS

| | | | |
|---|---|---|---|
| 2008/0294096 A1 | 11/2008 | Uber et al. | |
| 2013/0336814 A1* | 12/2013 | Kamen | A61M 5/1411 417/302 |
| 2014/0074030 A1* | 3/2014 | Hung | A61M 5/16831 604/152 |
| 2015/0217051 A1* | 8/2015 | Mastrototaro | A61M 5/14248 604/504 |
| 2016/0175510 A1* | 6/2016 | Patel | G05D 16/2066 137/12 |
| 2017/0120040 A1* | 5/2017 | Burkholz | A61M 39/288 |
| 2017/0354777 A1* | 12/2017 | Ofek | A61M 1/80 |
| 2018/0099090 A1* | 4/2018 | Miyamoto | A61M 5/16831 |
| 2018/0364086 A1* | 12/2018 | Farinella | A61M 5/172 |

FOREIGN PATENT DOCUMENTS

| | | | |
|---|---|---|---|
| WO | 2017/063930 | 4/2017 | |
| WO | WO-2017063930 A1 * | 4/2017 | A61M 39/28 |
| WO | WO-2017184777 A1 * | 10/2017 | |

* cited by examiner

CATHETER SYSTEM CLAMP, SYSTEMS, AND METHODS

RELATED APPLICATIONS

This application claims the benefit of U.S. Application No. 62/830,838, filed Apr. 8, 2019, and entitled CATHETER SYSTEM CLAMP, SYSTEMS, AND METHODS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral IV catheter ("PIVC"). As its name implies, the over-the-needle PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the PIVC in place for future blood withdrawal and/or fluid infusion.

In some instances, the PIVC may become unusable or compromised be due to occlusion of the PIVC over time. In response to the PIVC becoming occluded, the PIVC may need to be removed and replaced with a new catheter. Catheter occlusions may be thrombotic, resulting from formation of a thrombus within or surrounding a distal tip of the catheter. Catheter occlusions may also be non-thrombotic, resulting from precipitates, mechanical obstructions, and other factors. Further, catheter occlusions can lead to catheter infection, pulmonary embolism, post-thrombotic syndrome, and other negative health outcomes. Clinicians are instructed to regularly flush the PIVC to prevent occlusion and extend an indwelling period of the PIVC but some may fail to follow flushing protocols.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems and related devices and methods. In some embodiments, a method to manage flushing of a catheter assembly may include providing a clamp for a fluid tube configured to couple to the catheter assembly. In some embodiments, the clamp may include a sensor configured to detect when the clamp is closed. In some embodiments, the method may include starting a timer in response to the sensor detecting the clamp is closed. In some embodiments, the method may include providing an alert in response to the timer reaching a predetermined duration of time. In some embodiments, the alert may indicate to a clinician that the catheter assembly should be opened and flushed, which may prevent occlusion of the catheter assembly.

In some embodiments, providing the alert may include transmitting an alert signal over a network to a monitoring device, such as a clinician monitoring device. In some embodiments, the alert signal may indicate to the monitoring device to provide the alert. In some embodiments, the alert may include a sound, a tactile vibration, or a visual cue. In some embodiments, the visual cue may include a change in status of a light. In some embodiments, an indication may be provided in an electronic health record of a patient in response to the sensor detecting the clamp is closed.

In some embodiments, the sensor may be configured to detect the clamp is open. In some embodiments, in response to the sensor detecting the clamp is open for another predetermined duration of time, the timer may be stopped and/or reset. In some embodiments, in response to the sensor detecting the clamp is open for the other predetermined duration of time, another alert signal may be transmitted over the network to the monitoring device to stop the alert or provide another alert. In some embodiments, another indication may be provided in the electronic health record of the patient in response to the sensor detecting the clamp is open for the other predetermined duration of time.

In some embodiments, another sensor may be provided, which may be configured to detect fluid flowing through the fluid tube. In some embodiments, the other sensor may include a flow sensor. In some embodiments, in response to the sensor detecting the clamp is open and the other sensor detecting fluid flowing through the fluid tube, the timer may be stopped and/or reset.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
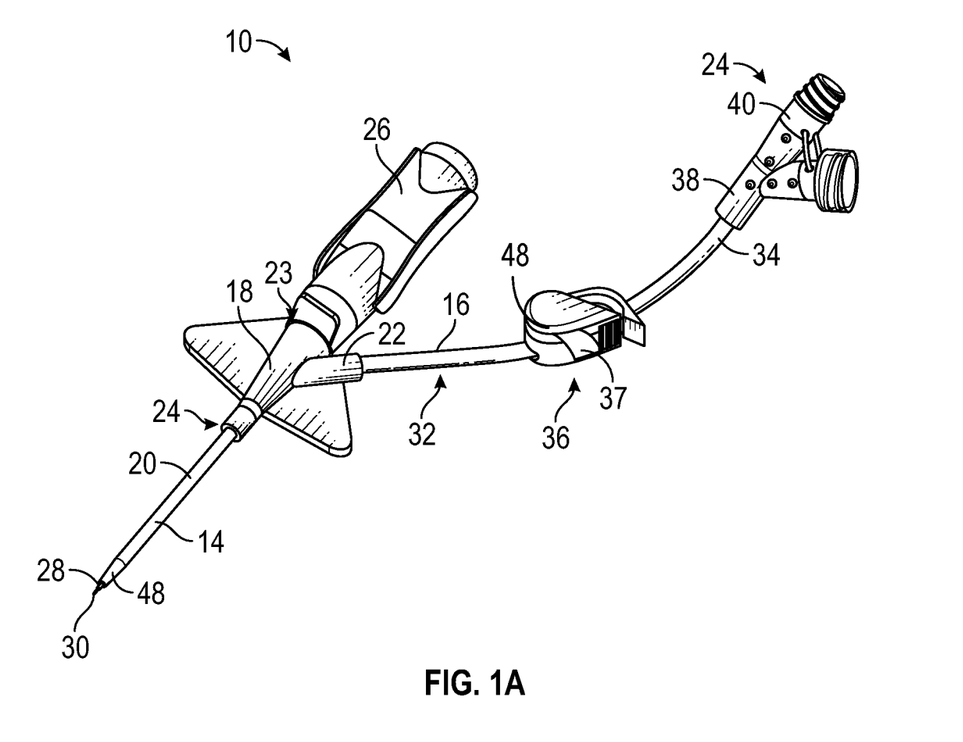
FIG. 1A is an upper perspective view of an example catheter system, according to some embodiments.

Referring now to FIG. 1A, an example catheter system 14 is illustrated, according to some embodiments. In some embodiments, the catheter system 14 may include a catheter assembly 16. In some embodiments, the catheter assembly 16 may include a catheter adapter 18 and a catheter 20 extending distally from the catheter adapter 18. In some embodiments, the catheter adapter 18 may include a side port 22 in fluid communication with the lumen of the catheter adapter 18. In some embodiments, the catheter adapter 18 may include a proximal end 23, a distal end 24, and a lumen extending there between. In some embodiments, the catheter 20 may include a PIVC.

In some embodiments, the catheter assembly 16 may be removably coupled to a needle assembly, which may include a needle hub 26 and an introducer needle 28. In some embodiments, the introducer needle 28 may include a sharp distal tip 30. In some embodiments, a proximal end of the introducer needle 28 may be secured within the needle hub 26. In some embodiments, the introducer needle 28 may extend through the catheter 20 when the catheter assembly 16 is in an insertion position ready for insertion into vasculature of a patient, as illustrated, for example, in FIG. 1A. In some embodiments, in response to the introducer needle 28 being inserted into the vasculature of the patient, flashback of blood may flow through the sharp distal tip 30 of the introducer needle 28 and may be visible to a clinician between the introducer needle 28 and the catheter 20 and/or at another location within the catheter assembly 16.

In some embodiments, in response to confirmation via the blood flashback that the catheter 20 is positioned within vasculature of the patient, the needle assembly may be removed from the catheter assembly 16. In some embodiments, when the needle assembly is coupled to the catheter assembly 16, as illustrated, for example, in FIG. 1A, the introducer needle 28 of the needle assembly may extend through a septum disposed within the lumen of the catheter adapter 18.

In some embodiments, the catheter system 14 may include one or more fluid tubes. In some embodiments, the fluid tubes may include any suitable tube through which fluid may flow to enter the catheter assembly 16. In some embodiments, the catheter system 14 may include a clamp 36 through which a particular fluid tube may extend. In some embodiments, the fluid tubes may be connected to each other and/or one or more other elements to form a fluid pathway that extends between an IV bag or a fluid delivery device and the catheter assembly 16.

In some embodiments, the fluid tubes may include an extension tube 34, which may be coupled with the catheter assembly 16. In further detail, in some embodiments, a distal end of the extension tube 34 may be integrated with the catheter adapter 18, as illustrated, for example, in FIG. 1A. For example, the extension tube 34 may be integrated with the side port 22 of the catheter adapter 18. In some embodiments, the extension tube 34 may be removably coupled to the catheter adapter 18. In some embodiments, the fluid tubes may include another tube, which may be disposed proximal to the extension tube 34. For example, the other tube may be coupled to the IV bag or the fluid delivery device. In some embodiments, the other tube may include an IV line that may extend between the IV bag and the extension tube 24.

In some embodiments, the clamp 36 may selectively close off the particular fluid tube on which the clamp is disposed to prevent blood or another fluid from flowing through the particular fluid tube. In some embodiments, the clinician may activate the clamp 36 by removing a battery isolator 37 or flipping a switch.

In some embodiments, an adapter 38 may be coupled to a proximal end of the extension tube 34. In some embodiments, the adapter 38 may include a Y-adapter or another suitable connector. In some embodiments, a needleless connector 40 may be coupled to the adapter 38. In some embodiments, the adapter 38 and/or the needleless connector 40 may be used to connect the catheter 20 with a medical device for fluid administration or blood withdrawal. The medical device may include a transfusion bag, syringe, or any other suitable medical device.

In some embodiments, the catheter system 14 may include any suitable catheter assembly, and the clamp 36 may be coupled to any suitable fluid tube. In some embodiments, the extension tube 34 may extend from the proximal end 23 of the catheter adapter 18. In some embodiments, the catheter assembly 16 may include a peripheral, central, or midline catheter assembly. In some embodiments, a peripherally inserted central catheter ("PICC") assembly may include pigtail extension tubes, and a particular clamp 36 may be coupled to one or more of the pigtail extension tubes.

Figure 1B:
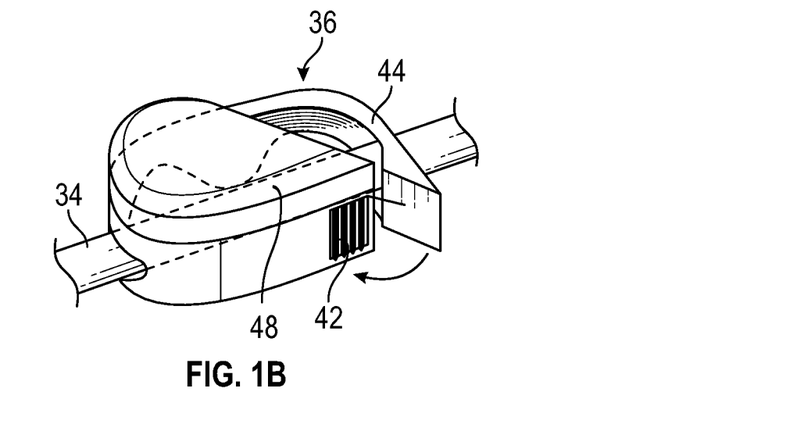
FIG. 1B is an upper perspective view of an example clamp, illustrating the clamp in an open position, according to some embodiments.

Referring now to FIG. 1B, in response to the clamp 36 being opened, fluid may flow through the fluid tubes, such as, for example, the extension tube 34 and/or the other fluid tube, and through the catheter assembly 16. For example, fluid may be infused into the patient via a medical device coupled to the adapter 38 or blood may be withdrawn from the patient into a blood collection device coupled to the adapter 38. In some embodiments, the clamp 36 may include a sensor 42, which may be configured to detect the clamp 36 is closed and/or open. In some embodiments, the sensor 42 may be positioned to detect movement of the clamp 36.

In some embodiments, the sensor 42 may include an optical sensor, a magnetic sensor, an electro-mechanical sensor, or another suitable type of sensor. As an example, the optical sensor may include a light barrier, which may be realized by a light emitting diode or a laser diode and a phototransistor. As an example, the magnetic sensor may include a reed relay or Hall sensor. As an example, the electromechanical sensor may include a switch or potentiometer.

Figure 1C:
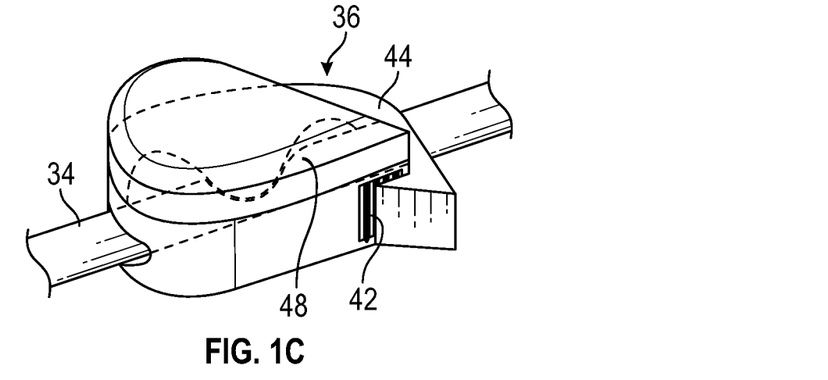
FIG. 1C is an upper perspective view of the clamp of FIG. 1B, illustrating the clamp is a closed position, according to some embodiments.

Referring now to FIG. 1C, in response to the clamp 36 being closed, fluid may be prevented from flowing through the particular fluid tube on which the clamp 36 is disposed. In some embodiments, the clamp 36 may include a pinch clamp, which may pinch the particular fluid tube in response to movement of the clamp 36 to the closed position. In some embodiments, the clamp 36 may include an arm 44, which may include a protrusion that contacts and pinches the particular fluid tube. In some embodiments, the clamp 36 may include any suitable clamp, and the sensor 42 may include any suitable sensor. In some embodiments, the sensor 42 may be disposed at various locations.

In some embodiments, the clamp 36 may provide an alert which may include a sound, a tactile vibration, or a visual cue. In some embodiments, the visual cue may include a change in status of a light. FIGS. 1A-1C illustrate an example light 48, according to some embodiments. In some embodiments, the status of the light 48 may change in response to the clamp 36 being closed for a predetermined duration of time. For example, the light 48 may turn on or may change color in response to the clamp 36 being closed for the predetermined duration of time. As another example, the light 48 may blink or change a rate of blinking in response to the clamp 36 being closed for the predetermined duration of time.

In some embodiments, the predetermined duration of time may correspond to a time prior to a clinically recommended time to flush the catheter assembly 16. In these embodiments, the alert may include a warning, which may indicate to the clinician that a clinically recommended time to flush the catheter assembly 16 is approaching. In some embodiments, the clinically recommended time to flush the catheter assembly 16 may be between about 6 hours and about 8 hours from the previous flushing of the catheter assembly 16. In some embodiments, the predetermined duration of time may correspond to the clinically recommended time to flush the catheter assembly 16. In some embodiments, a first alert may be provided by the clamp 36 in response to the clinically recommended time to flush the catheter assembly 16 approaching (such as, for example, in 30 minutes, 10 minutes, or 5 minutes), and a second alert may be provided by the clamp 36 in response to arrival of the clinically recommended time to flush the catheter assembly 16. In some embodiments, the first alert may include a yellow or orange light, and the second alert may include a red light.

In some embodiments, the light 48 may be disposed at various locations on the clamp 36, which may be visible to the clinician. In some embodiments, the clamp 36 may include multiple lights 48. In some embodiments, the light 48 may extend around a curved edge of the clamp 36, as illustrated, for example, in FIGS. 1A-1C.

Figure 1D:
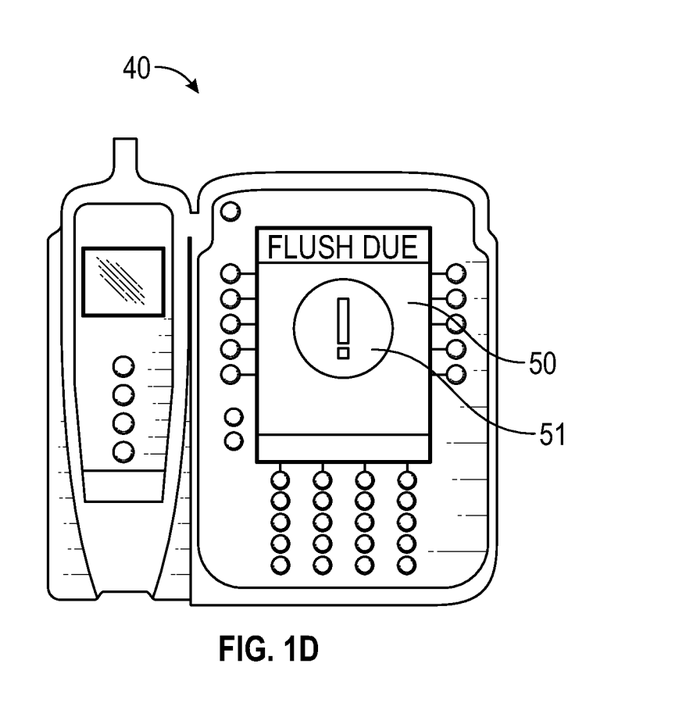
FIG. 1D is an upper perspective view of an example clinician monitoring device, according to some embodiments.

Referring now to FIG. 1D, an example clinician monitoring device 46 is illustrated, according to some embodiments. Examples of the clinician monitoring device 46 may include a computing device, a mobile phone, a smartphone, a tablet computer, a laptop computer, a desktop computer, a medical device, or a connected device (e.g., a smartwatch, smart glasses, or any other connected device). In some embodiments, in addition to the clamp 36 or as an alternative to the clamp 36, the clinician monitoring device 46 may provide the alert.

In some embodiments, the clinician monitoring device 46 may include a display screen 50, which may provide the alert. In some embodiments, the alert may include a phrase such as, for example, "Flush Due." In some embodiments, the alert may include a visual cue on the display screen 50, such as a portion 51 of the display screen 50 that lights up or changes color. In some embodiments, the portion 51 of the display screen 50 may blink or change a rate of blinking to provide the alert. In some embodiments, the clinician monitoring device 46 may include the light 48, as described, for example, with respect to FIG. 1C.

Figure 1E:
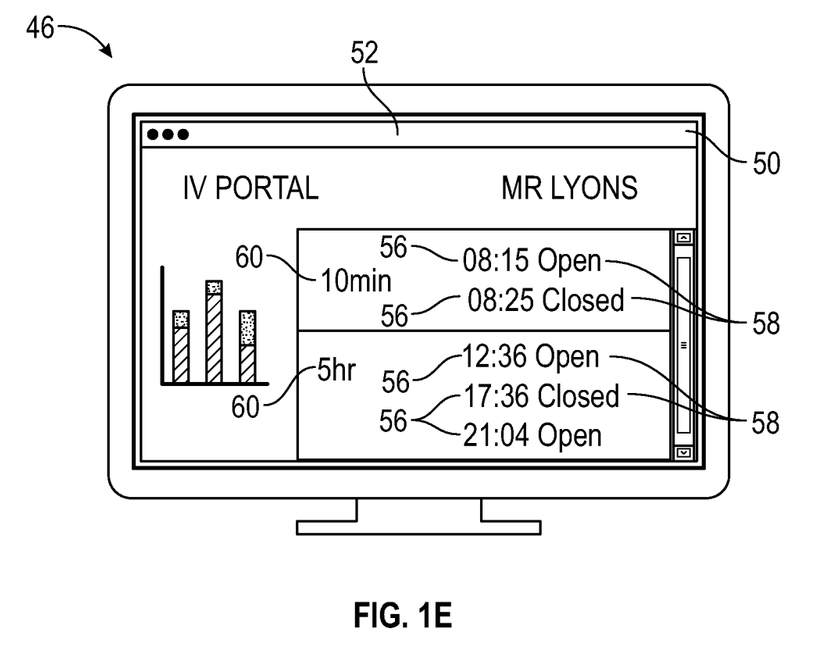
FIG. 1E is an example electronic health record that may be presented on a display screen of a clinician monitoring device, according to some embodiments.

Referring now to FIG. 1E, an example electronic health record 52 that may be presented on the display screen 50 of the clinician monitoring device 46 is illustrated, according to some embodiments. In some embodiments, an indication may be provided on the display screen 50 in response to opening and/or closing of the clamp 36. In some embodiments, the indication may be provided on the display screen 50 in response to opening the clamp 36 for a particular predetermined duration of time and/or closing the clamp 36 for a particular predetermined duration of time.

In some embodiments, the indication may include one or more of the following: a time of day 56, a status 58, and a duration of time 60. In some embodiments, the duration of time 60 may include a duration of time the clamp 36 has been closed. In some embodiments, the status 58 may include "open" and may be adjacent to the time of day 56, indicating to the clinician the time of day at which the clamp 36 was opened. In some embodiments, the status 58 may include "closed" and may be adjacent to the time of day 56, indicating to the clinician the time of day at which the clamp 36 was closed.

Figure 2:
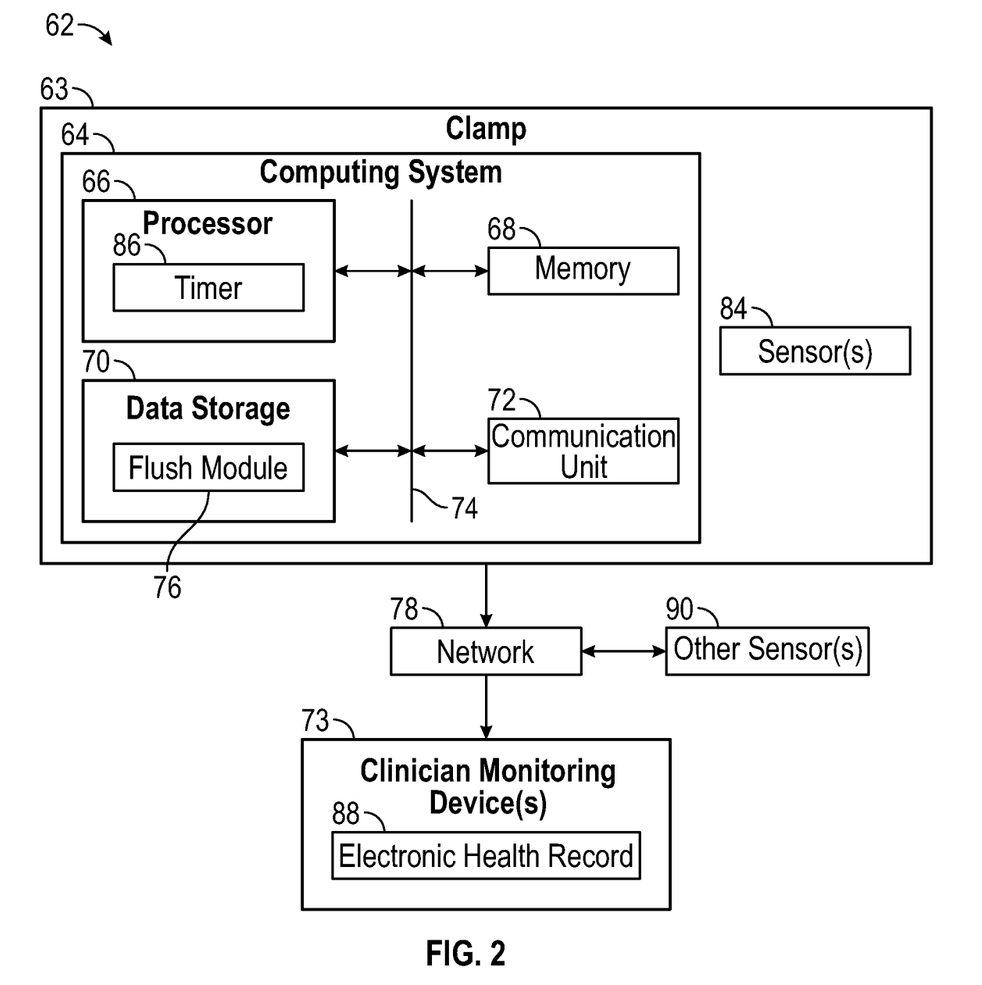
FIG. 2 is a block diagram of an example flush management system, according to some embodiments.

FIG. 2 is as block diagram of an example flush management system (FM system) 62, arranged in accordance with at least one embodiment described in the present disclosure. In some embodiments, the FM system 62 may include the clamp 63. In some embodiments, the clamp 63 may include or correspond to the clamp 36 described with respect to FIG. 1. In some embodiments, the clamp 63 may include a computing system 64.

In some embodiments, the computing system 64 may include a processor 66, a memory 68, a data storage 70, and a communication unit 72. In some embodiments, the processor 66, the memory 68, the data storage 70, and the communication unit 72 may be communicatively coupled by a bus 74. The bus 74 may include, but is not limited to, a controller area network (CAN) bus, a memory bus, a storage interface bus, a bus/interface controller, an interface bus, or the like or any combination thereof. In some embodiments, the processor 66 may include a timer 75. In some embodiments, the timer 75 may be a separate component linked to the processor 66.

In general, the processor 66 may include any suitable special-purpose or general-purpose computer, computing entity, or processing device including various computer hardware or software modules and may be configured to execute instructions stored on any applicable computer-readable storage media. For example, the processor 66 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Although illustrated as a single processor in FIG. 2, the processor 66 may include any number of processors configured to perform, individually or collectively, any number of operations described in the present disclosure. Additionally, one or more of the processors 66 may be present on one or more different electronic devices.

In some embodiments, the processor 66 may interpret and/or execute program instructions and/or process data stored in the memory 68, the data storage 70, or the memory 68 and the data storage 70. In some embodiments, the processor 66 may fetch program instructions from the data storage 70 and load the program instructions in the memory 68. In some embodiments, after the program instructions are loaded into memory 68, the processor 66 may execute the program instructions.

For example, in some embodiments, a flush module 76 may be included in the data storage 70 as program instructions. In some embodiments, the flush module 76 may be configured to manage flushing of the catheter line 32 and the catheter assembly 16. The processor 66 may fetch the program instructions of the flush module 76 from the data storage 70 and may load the program instructions of the flush module 76 in the memory 68. After the program instructions of the flush module 76 are loaded into the memory 68, the processor 66 may execute the program instructions such that the computing system 64 may implement the operations associated with the flush module 76 as directed by the instructions.

The memory 68 and the data storage 70 may include computer-readable storage media for carrying or having computer-executable instructions or data structures stored thereon. Such computer-readable storage media may include any available media that may be accessed by a general-purpose or special-purpose computer, such as the processor 66. By way of example, and not limitation, such computer-readable storage media may include tangible or non-transitory computer-readable storage media including RAM, ROM, EEPROM, CD-ROM or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 66 to perform a certain operation or group of operations.

In some embodiments, one or more clinician monitoring devices 73 may be connected to the computing system 64 via a network 78. In these and other embodiments, the network 78 may include a wired or wireless network, and may have any suitable configuration, such as a star configuration, a token ring configuration, or other configurations. Furthermore, in some embodiments, the network 78 may include an Ethernet network, a local area network (LAN), a wide area network (WAN) (e.g., the Internet), and/or other interconnected data paths across which multiple devices may communicate. In some embodiments, the network 78 may include a peer-to-peer network. In some embodiments, the network 78 may also be coupled to or include portions of a telecommunications network that may enable communication of data in a variety of different communication protocols. In some embodiments, the clinician monitoring devices 73 may include or correspond to any of the clinician monitoring devices 46 described with respect to FIG. 1.

In some embodiments, the network 78 may include BLUETOOTH® communication networks and/or cellular communications networks for sending and receiving data including via short messaging service (SMS), multimedia messaging service (MMS), hypertext transfer protocol (HTTP), direct data connection, wireless application protocol (WAP), e-mail, etc. The network 78 may enable communication via a standard-based protocol such as smart energy profile (SEP), Echonet Lite, OpenADR, or another suitable protocol (e.g., wireless fidelity (Wi-Fi), ZigBee, HomePlug Green, etc.).

In some embodiments, the communication unit 72 may be configured to transmit data to and receive data from the clinician monitoring devices 73 via the network 78. In some embodiments, the communication unit 72 may also be configured to transmit and receive data from a display screen 80 and/or an electronic health record 82. In some embodiments, the display screen 80 may include or correspond to the display screen 50 described with respect to FIG. 1D or 1E. In some embodiments, the electronic health record 82 may include or correspond to the electronic health record 52 of FIG. 1E. In some embodiments, the flush module 76 may be configured to send and receive data via the communication unit 72.

In some embodiments, the communication unit 72 may include a port for direct physical connection to the network 78 and/or another communication channel. For example, the communication unit 72 may include a universal serial bus (USB) port, a secure digital (SD) port, a category 5 cable (CAT-5) port, or similar port for wired communication with another device. In some embodiments, the communication unit 72 may include a wireless transceiver for exchanging data with the clinician monitoring device 46 or other communication channels using one or more wireless communication methods, including IEEE 802.11, IEEE 802.16, BLUETOOTH®, or another suitable wireless communication method.

In some embodiments, the communication unit 72 may include a cellular communications transceiver for sending and receiving data over a cellular communications network including via SMS, MMS, HTTP, direct data connection, WAP, e-mail, or another suitable type of electronic communication. The communication unit 72 may also provide other conventional connections to the network 78 for distribution of files or media objects using standard network protocols including transmission control protocol/internet protocol (TCP/IP), HTTP, HTTP secure (HTTPS), and simple mail transfer protocol (SMTP).

An example of how the flush module 76 may manage flushing of a catheter assembly is now provided. In some embodiments, in response to a sensor 84 detecting the clamp is closed, the flush module 76 may be configured to start a timer 86. In some embodiments, the sensor 84 may include or correspond to the sensor 42 described with respect to FIG. 1. In some embodiments, in response to the timer 86 reaching a predetermined duration of time, the flush module 76 may be configured to generate one or more alerts at the clamp and/or to transmit an alert signal over the network 78 to the clinician monitoring devices 73, which may provide one or more alerts. In some embodiments, the alerts may include any of the alerts described with respect to FIG. 1. In some embodiments, the alerts may indicate to the clinician that the clinically recommended time to flush the catheter assembly has arrived or is approaching.

In some embodiments, the flush module 76 may be configured to provide an indication in an electronic health record 88 of a patient in response to the sensors 84 detecting the clamp 63 is closed. In some embodiments, the electronic health record 88 may be stored and/or displayed on the clinician monitoring devices 73. In some embodiments, the electronic health record 88 may include or correspond to the electronic health record 52 described with respect to FIG. 1. In some embodiments, the indication may include or correspond to the indication 54 described with respect to FIG. 1.

In some embodiments, in response to the sensors 84 detecting the clamp 63 is open or open for another predetermined duration of time, the flush module 76 may be configured to stop and/or reset the timer 86. In some embodiments, the flush module 76 may be configured to stop the timer 86 only after the clamp 63 has been open for the other predetermined duration of time to prevent opening of the clamp 63 when adequate flushing could not have occurred.

In some embodiments, in response to the sensors 84 detecting the clamp 63 is open for the other predetermined duration, the flush module 76 may be configured to stop the alert at the clamp 63 or provide a different alert at the clamp 63. Additionally or alternatively, in some embodiments, in response to the sensors 84 detecting the clamp 63 is open for the other predetermined duration, the flush module 76 may be configured to transmit another alert signal over the network 78 to the clinician monitoring devices 73 to stop the alert or provide a different alert.

In some embodiments, the flush module 76 may be configured to provide another indication in the electronic health record 88 of the patient in response to the sensors 84 detecting the clamp 63 is open for the other predetermined duration of time. In some embodiments, the other indication may include or correspond to the indication 54 described with respect to FIG. 1.

In some embodiments, one or more other sensors 90 may be configured to detect fluid flowing through a fluid tube, such as, for example the extension tube 34 of the catheter assembly 16 described with respect to FIG. 1 or another fluid tube in fluid communication with the catheter assembly 16. In some embodiments, the other sensors may include a flow sensor and/or a pressure sensor. Example devices that include flow sensors and/or pressure sensors are described in U.S. Patent Application No. 62/830,707, filed Apr. 8, 2019, entitled "OCCLUSION DETECTION DEVICES, SYSTEMS, AND METHODS," and U.S. Pat. No. 5,533,412, filed Jun. 7, 1995, entitled "PULSED THERMAL FLOW SENSOR SYSTEM," which are hereby incorporated by reference in their entirety. In some embodiments, in response to the sensors 84 detecting the clamp 63 is open and the other sensors 90 detecting fluid flowing through the fluid tube, the flush module 76 may be configured to stop and/or reset the timer 86. Although illustrated outside the clamp 63 in FIG. 2, it is understood that the other sensors 90 may be part of the clamp 63.

In some embodiments, an external server may include one or more components of the computing system 64. In some embodiments, the external server may be connected to the clamp 63 and/or the clinician monitoring device 73 via the network 78 or another network. Modifications, additions, or omissions may be made to the FM system 62 without departing from the scope of the present disclosure.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A method to manage flushing of a catheter assembly, the method comprising:
   providing a clamp for a fluid tube, wherein the fluid tube is configured to couple to a catheter assembly, wherein the clamp comprises a sensor configured to detect the clamp is closed;
   in response to the sensor detecting the clamp is closed, starting a timer;
   in response to the timer reaching a predetermined duration of time, providing an alert; and
   in response to the timer reaching another predetermined duration of time, providing another alert, wherein the other predetermined duration of time is greater than the predetermined duration of time and corresponds to a time to flush the catheter assembly.

2. The method of claim 1, wherein providing the alert comprises transmitting an alert signal over a network to a monitoring device, wherein the alert signal indicates to the monitoring device to provide the alert.

3. The method of claim 1, wherein the alert comprises a sound, a tactile vibration, or a visual cue.

4. The method of claim 1, further comprising providing an indication in an electronic health record of a patient in response to the sensor detecting the clamp is closed.

5. The method of claim 1, wherein the sensor is configured to detect the clamp is open, further comprising in response to the sensor detecting the clamp is open for another predetermined duration of time, stopping or resetting the timer.

6. The method of claim 5, further comprising in response to the sensor detecting the clamp is open for the other predetermined duration of time, transmitting another alert signal over a network to a monitoring device, wherein the other alert signal indicates to the monitoring device to stop the alert or provide another alert.

7. The method of claim 6, further comprising providing an indication in an electronic health record of a patient in response to the sensor detecting the clamp is open for the other predetermined duration of time.

8. The method of claim 1, further comprising providing an indication in an electronic health record of a patient in response to the timer reaching the predetermined duration of time.

9. The method of claim 1, wherein the alert comprises a sound emanating from the clamp or a change in status of a light coupled to the clamp.

10. The method of claim 1, wherein the other predetermined duration of time is between about six hours and about eight hours.

11. A method to manage flushing of a catheter assembly, the method comprising:
    providing a clamp for a fluid tube, wherein the fluid tube is configured to couple to a catheter assembly, wherein the clamp comprises a first sensor configured to detect the clamp is open;
    providing a second sensor configured to detect fluid flowing through the fluid tube;
    in response to the first sensor detecting the clamp is open and the second sensor detecting fluid flowing through the fluid tube, stopping or resetting a timer, wherein the clamp is configured to provide an alert in response to the timer reaching a predetermined duration of time.

12. The method of claim 11, wherein the second sensor comprises a flow sensor.

13. The method of claim 11, further comprising in response to the first sensor detecting the clamp is closed, starting the timer.

14. The method of claim 11, wherein the alert comprises a sound, tactile vibration, or a visual cue.

15. The method of claim 11, further comprising providing an indication in an electronic health record of a patient in response to the first sensor detecting the clamp is open and the second sensor detecting fluid flowing through the fluid tube.

* * * * *